US008618179B2

(12) United States Patent
Klingelhoefer et al.

(10) Patent No.: US 8,618,179 B2
(45) Date of Patent: Dec. 31, 2013

(54) COMPOSITION COMPRISING A PESTICIDE AND AN ALKOXYLATE OF 2-PROPYLHEPTYLAMINE

(75) Inventors: Paul Klingelhoefer, Mannheim (DE); Arend Jouke Kingma, Ludwigshafen (DE); Sophie Vogel, Mannheim (DE); Kevin Huyghe, Mannheim (DE); Gerd Haderlein, Grünstadt (DE); Gerhard Schnabel, Elsenfeld (DE); Marc Nolte, Mannheim (DE); Richard Roger Evans, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/007,187

(22) Filed: Jan. 14, 2011

(65) Prior Publication Data

US 2011/0177945 A1     Jul. 21, 2011

Related U.S. Application Data

(60) Provisional application No. 61/295,784, filed on Jan. 18, 2010.

(30) Foreign Application Priority Data

Mar. 23, 2010 (EP) .................................. 10157267

(51) Int. Cl.
| | |
|---|---|
| *A01N 33/08* | (2006.01) |
| *A01N 33/12* | (2006.01) |
| *A01N 57/18* | (2006.01) |
| *A01N 25/00* | (2006.01) |
| *A01N 25/02* | (2006.01) |
| *A61K 47/00* | (2006.01) |
| *C07C 213/00* | (2006.01) |
| *C07C 215/00* | (2006.01) |
| *C07C 217/00* | (2006.01) |
| *C07C 209/00* | (2006.01) |

(52) U.S. Cl.
USPC ........... 514/668; 514/669; 514/642; 514/788; 504/206; 504/358; 504/362; 564/294; 564/478; 564/503; 564/505; 564/508

(58) Field of Classification Search
USPC .......... 514/668, 669, 642, 788; 504/206, 358, 504/362; 564/294, 478, 503, 505, 508
See application file for complete search history.

(56) References Cited

U.S. PATENT DOCUMENTS

| | | | |
|---|---|---|---|
| 5,530,127 A | 6/1996 | Reif et al. | |
| 5,668,085 A | 9/1997 | Forbes et al. | |
| 5,750,468 A | 5/1998 | Wright et al. | |
| 2002/0016264 A1 | 2/2002 | Shannon et al. | |
| 2002/0137634 A1 | 9/2002 | Krause et al. | |
| 2006/0019828 A1 | 1/2006 | Becher et al. | |
| 2008/0261814 A1* | 10/2008 | Zhu et al. ...................... | 504/206 |
| 2009/0114879 A1 | 5/2009 | Hellsten et al. | |
| 2009/0286684 A1 | 11/2009 | Scherl et al. | |
| 2010/0317521 A1* | 12/2010 | Correia .......................... | 504/206 |
| 2011/0039703 A1* | 2/2011 | Correia .......................... | 504/206 |
| 2011/0201497 A1 | 8/2011 | Klingelhoefer et al. | |
| 2011/0230342 A1 | 9/2011 | Klingelhoefer et al. | |

FOREIGN PATENT DOCUMENTS

| | | |
|---|---|---|
| DE | 10 2005 037 971 | 2/2007 |
| EP | 0 696 572 | 2/1996 |
| WO | WO 01/97614 | 12/2001 |
| WO | WO 2006/034459 | 3/2006 |
| WO | WO 2007/030312 | 3/2007 |
| WO | WO 2009/004044 | 1/2009 |
| WO | WO 2011/104211 | 9/2011 |

OTHER PUBLICATIONS

Tsui, Martin T.K., et al. "Aquatic toxicity of glyphosate-based formulations: comparison between difference organisms and the effects of environmental factors", Chemosphere, 2003, p. 1189-1197, vol. 52.
European Search Report prepared in corresponding European Application.
Office Action dated Jan. 30, 2013, in U.S. Appl. No. 13/048,946.

* cited by examiner

*Primary Examiner* — John Pak
*Assistant Examiner* — Nathan W Schlientz
(74) *Attorney, Agent, or Firm* — Brinks Gilson & Lione

(57) ABSTRACT

The present invention relates to a composition comprising a pesticide and an alkoxylate. Moreover, the invention relates to the alkoxylate, to a process for its preparation and to its use as adjuvant in pesticide-comprising spray mixtures. The invention furthermore relates to a method of controlling phytopathogenic fungi and/or undesired vegetation and/or undesired insect or mite attack and/or for regulating the growth of plants, wherein the composition is allowed to act on the respective pests, their environment or the plants to be protected from the respective pest, on the soil and/or on undesirable plants and/or the crop plants and/or their environment. Furthermore, the invention relates to seed comprising the composition.

13 Claims, No Drawings

COMPOSITION COMPRISING A PESTICIDE AND AN ALKOXYLATE OF 2-PROPYLHEPTYLAMINE

The present patent document claims the benefit of the filing date under 35 U.S.C. §119(e) of Provisional U.S. Patent Application Ser. No. 61/295,784, filed Jan. 18, 2010, which is hereby incorporated by reference. This application also claims priority under 35 U.S.C. §119 to European Patent Application No. 10157267.5, filed Mar. 23, 2010, the entire contents of which is hereby incorporated herein by reference.

The present invention relates to a composition comprising a pesticide and an alkoxylate. Moreover, the invention relates to the alkoxylate, to a process for its preparation and to its use as adjuvant in pesticide-comprising spray mixtures. The invention furthermore relates to a method of controlling phytopathogenic fungi and/or undesired vegetation and/or undesired insect or mite attack and/or for regulating the growth of plants, wherein the composition is allowed to act on the respective pests, their environment or the plants to be protected from the respective pest, on the soil and/or on undesirable plants and/or the crop plants and/or their environment. Furthermore, the invention relates to seed comprising the composition. The present invention comprises combinations of preferred features with other preferred features.

Alkoxylates and their use in agrochemical formulations as adjuvants are generally known:

WO 2009/004044 discloses a herbicidal composition comprising a phenoxy-acid herbicide and an alkoxylated alkylamine as adjuvant, it being possible for the alkylamine, for example, to be a 2-propylheptylmethylamine which is alkoxylated with 3 to 20 ethylene oxide groups.

U.S. Pat. No. 5,668,085 discloses a herbicidal composition comprising an aqueous solution of glyphosate and surfactant. The surfactant may be an alkoxylated alkylamine, the alkyl group comprising 8 to 22 carbon atoms.

Alkoxylated alkylamines, in particular commercially available ethoxylated tallow fatty amines (POEA), have important toxic properties (such as irritation of the skin and the eyes) and ecotoxic properties (such as high ecotoxicity to aquatic organisms such as algae and daphnias). Thus, for example, POEA (CAS No. 61791-26-2), which is frequently present in Roundup® herbicides as a wetter, is considered to be relatively toxic to aquatic organisms (Tsuí and Chu, Chemosphere 2003, 52, 1189-1197).

It was therefore an object of the present invention to find an adjuvant which is well suited to herbicides such as glyphosate while being less toxic (especially lower toxicity to aquatic organisms). Furthermore, the adjuvant should make possible a storage-stable formulation of the pesticides.

The object was solved by a composition comprising a pesticide and an alkoxylate, wherein the alkoxylate is an amine alkoxylate (A)

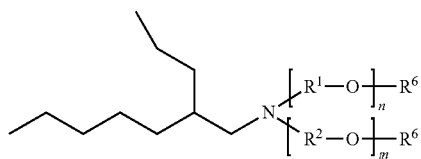

(A)

or a quaternized derivative (AQ)

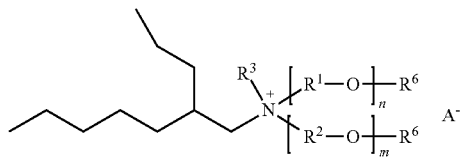

(AQ)

of the amine alkoxylate (A), where
$R^1$, $R^2$, and $R^5$ independently of one another are ethylene, propylene, butylene or a mixture of these,
$R^3$ is an H, —OH, —OR$^4$, —[R$^5$—O]$_p$—R$^6$, $C_1$-$C_6$-alkyl or an oxygen anion,
$R^4$ is a $C_1$-$C_6$-alkyl, $C_2$-$C_6$-alkenyl or $C_2$-$C_6$-alkynyl,
$R^6$ is an H, $C_1$-$C_6$-alkyl, $C_2$-$C_6$-alkenyl, $C_2$-$C_6$-alkynyl, —SO$_3$R$^a$, —P(O)OR$^b$OR$^c$, —CH$_2$CO$_2$R$^d$, or —C(O)R$^e$,
$R^a$ and $R^d$ independently of one another are an H, inorganic or organic cations,
$R^b$ and $R^c$ independently of one another are an H, inorganic or organic cations, $C_1$-$C_6$-alkyl, $C_2$-$C_6$-alkenyl or $C_2$-$C_6$-alkynyl,
$R^e$ is $C_1$-$C_{22}$-alkyl, $C_2$-$C_{22}$-alkenyl, $C_2$-$C_{22}$-alkynyl, $C_6$-$C_{22}$-aryl, $C_7$-$C_{22}$-alkylaryl,
n, m and p independently of one another have a value of from 1 to 30,
$A^-$ is an agriculturally acceptable anion, and, if $R^3$ is an oxygen anion, $A^-$ is absent.

Preferably, the composition according to the invention comprises a pesticide and an alkoxylate, wherein the alkoxylate is an amine alkoxylate (A).

Preferably, n has a value of from 1 to 20, especially preferably from 1 to 15. Preferably, m has a value of from 1 to 20, especially preferably from 1 to 15. Preferably, p has a value of from 1 to 30, especially preferably from 1 to 20. The values of n, m and o are normally average values as they mostly arise upon the alkoxylation with alkoxides. Therefore, n, m and o can not only be integers, but also all values between the integers.

Preferably, in the case of the amine alkoxylate (A), the total of n and m is 2 to 40 and in its quaternized derivative (AQ) the total of n, m and p is 3 to 80.

In the case of the amine alkoxylate (A) the total of n and m is especially preferably 3 to 30 and specifically 5 to 25. In a further especially preferred embodiment, the total of n and m is 6 to 9, in particular 6.5 to 8.5 and in particular 6.9 to 7.9. In a further especially preferred embodiment, the total of n and m is 11 to 40, in particular 12 to 30 and in particular 13.5 to 25. In a further especially preferred embodiment, the sum of n and m is 8 to 13, in particular 9 to 11.

In the case of the quaternized derivative (AQ) of the amine alkoxylate (A), the total of n, m and p is especially preferably 3 to 40 and specifically 5 to 25. In one especially preferred embodiment, the sum of n and m is 8 to 13, in particular 9 to 11.

$R^1$, $R^2$ and $R^5$ are preferably independently of one another ethylene, ethylene and propylene, ethylene and butylene, or ethylene, propylene and butylene. In a further preferred embodiment, $R^1$, $R^2$ and $R^5$ are propylene. In a further preferred embodiment, $R^1$, $R^2$ and $R^5$ are butylene. Especially preferably $R^1$, $R^2$ and $R^5$ independently of one another are ethylene, or ethylene and propylene. Very especially preferably, $R^1$, $R^2$ and $R^5$ are ethylene.

If $R^1$, $R^2$ or $R^5$ comprise a butylene radical, the latter may be present as a n-butylene, an isobutylene or a 2,3-butylene group, with n-butylene and isobutylene being preferred and n-butylene being most preferred.

$R^1$, $R^2$ and $R^5$ independently of one another may be a mixture of ethylene, propylene or butylene. In this context, for example one or all radicals $R^1$, $R^2$ and $R^5$ may comprise a mixture of these groups in each alkoxylate chain. Such mixtures can be linked to one another in any desired order, for example randomly or blockwise (such as one block ethylene and one block propylene). Also, it is possible for in each case one or more of the radicals $R^1$, $R^2$, and $R^5$ to form a complete alkoxylate chain composed of different alkylene groups. For example, $R^1$ and $R^2$ may be composed of ethylene and $R^5$ of propylene.

$R^3$ is preferably an H, —OH, $C_1$-$C_4$-alkyl or an oxygen anion, it is especially preferably an H, methyl, butyl or an oxygen anion. In a specifically preferred embodiment, $R^3$ is a methyl. In a further specifically preferred embodiment, $R^3$ is an oxygen anion. In a further specifically preferred embodiment, $R^3$ is an H.

$R^4$ is preferably a $C_1$-$C_6$-alkyl, in particular a methyl or butyl, especially butyl.

$R^6$ is preferably an H or $C_1$-$C_6$-alkyl, more preferably an H or methyl, especially H.

$R^a$ and $R^d$ are independently of one another H, or inorganic or organic cations, which may be singly or multiply positively charged. Examples of inorganic cations are cations of ammonium, $Na^+$, $K^+$, $Mg^{2+}$, $Ca^{2+}$, or $Zn^{2+}$. Examples of organic cations are methyl-ammonium, dimethylammonium, trimethylammonium, tetramethylammonium, (2-hydroxyethyl)ammonium, bis(2-hydroxyethyl)ammonium, tris(2-hydroxyethyl)-ammonium, tetra(2-hydroxyethyl)ammonium. Preferably, $R^a$ and $R^d$ independently of one another are H or inorganic cations. If an inorganic or organic cation is present, then the associated anionic group would be formed by the corresponding functional group (e.g., —$SO_3$—, —P(O)O$^-$O$^-$, or —$CH_2CO_2$—) on $R^6$.

$R^b$ and $R^c$ are preferably, independently of one another, H, inorganic or organic cations. Suitable inorganic or organic cations are those specified under $R^a$.

In another embodiment, in the quaternary derivative (AQ), the radicals $R^a$, $R^b$, $R^c$ and $R^d$ independently of one another may be organic cations, with the cationic group being the quaternary nitrogen cation of AQ itself. It would also be possible, therefore, for AQ to form a zwitterion, with the anionic group being formed by the corresponding functional group (e.g., —$SO_3$—, —P(O)O$^-$O$^-$, or —$CH_2CO_2$—) on $R^6$ in AQ, and the cationic group by the quaternary nitrogen of AQ. In this zwitterionic form of AQ, the presence of an agriculturally acceptable anion $A^-$ is optional.

$R^e$ is preferably $C_1$-$C_{12}$-alkyl, $C_6$-$C_{12}$-aryl, or $C_7$-$C_{12}$-alkylaryl, more preferably $C_1$-$C_6$-alkyl.

$A^-$ is an agriculturally acceptable anion, as they are generally known to the skilled worker. Preferably, $A^-$ is a halide (such as chloride or bromide), phosphate, sulfate or an anionic pesticide. Especially preferably, $A^-$ is an anionic pesticide, such as a glyphosate anion or glufosinate anion. If $R^3$ is an oxygen anion, an amine oxide is present. In this case, a further anion such as $A^-$ is absent.

In the case of the amine alkoxylate (A), it is preferred that $R^1$ and $R^2$ independently of one another are ethylene, ethylene and propylene, ethylene and butylene, or ethylene, propylene and butylene, and the total of n and m is 2 to 60, preferably 2 to 40, especially preferably 3 to 30 and in particular 5 to 25. In a further preferred embodiment, $R^1$ and $R^2$ are ethylene, ethylene and propylene, ethylene and butylene, or ethylene, propylene and butylene and the total of n and m is 6 to 9, in particular 6.5 to 8.5 and in particular 6.9 to 7.9 In a further preferred embodiment, $R^1$ and $R^2$ are ethylene, ethylene and propylene, ethylene and butylene, or ethylene, propylene and butylene and the total of n and m is 11 to 40, in particular 12 to 30 and in particular 13.5 to 25. In one particularly preferred embodiment, $R^1$ and $R^2$ are ethylene, ethylene and propylene, ethylene and butylene, or ethylene, propylene and butylene, and the sum of n and m is 6 to 14, more particularly 8 to 12, and especially 9 to 11.

In the case of the amine alkoxylate (A), it is especially preferred that $R^1$ and $R^2$ are ethylene, and the total of n and m is 2 to 60, preferably 2 to 40, especially preferably 3 to 30, and in particular 5 to 25. In a further especially preferred embodiment, $R^1$ and $R^2$ are ethylene and the total of n and m is 6 to 9, in particular 6.5 to 8.5 and in particular 6.9 to 7.9. In a further especially preferred embodiment, $R^1$ and $R^2$ are ethylene and the total of n and m is 11 to 40, in particular 12 to 30 and in particular 13.5 to 25.

The compounds (A) and (AQ) may be present as mixtures of stereoisomers or as isolated stereoisomers. Tautomers and betaines are likewise encompassed by the structures (A) and (AQ).

In most cases, the composition according to the invention comprises from 0.1 to 90% by weight of the alkoxylate, preferably from 1 to 50% by weight and in particular from 3 to 30% by weight.

The term pesticide refers to at least one active substance selected from the group of the fungicides, insecticides, nematicides, herbicides, safeners, molluscicides, rodenticides and/or growth regulators. Preferred pesticides are fungicides, insecticides, herbicides and growth regulators. Especially preferred pesticides are herbicides and growth regulators. Mixtures of pesticides from two or more of the above-mentioned classes may also be used. The skilled worker is familiar with such pesticides, which can be found, for example, in Pesticide Manual, 14th Ed. (2006), The British Crop Protection Council, London. Suitable pesticides are:

A) Strobilurins:
  azoxystrobin, dimoxystrobin, coumoxystrobin, coumethoxystrobin, enestroburin, fluoxastrobin, kresoximmethyl, metominostrobin, orysastrobin, picoxystrobin, pyraclostrobin, pyrametostrobin, pyraoxystrobin, pyribencarb, trifloxystrobin, methyl 2-[2-(2,5-dimethylphenyloxymethyl)phenyl]-3-methoxyacrylate, 2-(2-(3-(2,6-di-chlorophenyl)-1-methylallylideneaminooxymethyl)phenyl)-2-methoxyimino-N-methylacetamide;

B) Carboxamides:
  carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penflufen (N-(2-(1,3-dimethylbutyl)phenyl)-1,3-dimethyl-5-fluoro-1H-pyrazole-4-carboxamide), penthiopyrad, sedaxane, tecloftalam, thifluzamide, tiadinil, 2-amino-4-methylthiazole-5-carboxanilide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3,3-trimethylbutyl)-phenyl)-1,3-dimethyl-5-fluoro-1H-pyrazole-4-carboxamide;
  carboxylic acid morpholides: dimethomorph, flumorph, pyrimorph;
  benzamides: flumetover, fluopicolide, fluopyram, zoxamid;

other carboxamides: carpropamid, diclocymet, mandipropamid, oxytetracyclin, silthiofam, N-(6-methoxypyridin-3-yl)cyclopropanecarboxamide;

C) Azoles:
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole;
imidazoles: cyazofamid, imazalil, imazalil sulfate, pefurazoate, prochloraz, triflumizole;
benzimidazoles: benomyl, carbendazim, fuberidazole, thiabendazole;
others: ethaboxam, etridiazole, hymexazole, 2-(4-chlorophenyl)-N-[4-(3,4-dimethoxyphenyl)isoxazol-5-yl]-2-prop-2-ynyloxyacetamide;

D) Nitrogenous Heterocyclyl Compounds
pyridines: fluazinam, pyrifenox, 3-[5-(4-chlorophenyl)-2,3-dimethylisoxazolidin-3-yl]-pyridine, 3-[5-(4-methylphenyl)-2,3-dimethylisoxazolidin-3-yl]pyridine;
pyrimidines: bupirimate, cyprodinil, diflumetorim, fenarimol, ferimzone, mepanipyrim, nitrapyrin, nuarimol, pyrimethanil;
piperazines: triforine;
pyrroles: fludioxonil, fenpiclonil;
morpholines: aldimorph, dodemorph, dodemorph acetate, fenpropimorph, tridemorph;
piperidines: fenpropidin;
dicarboximides: fluorimid, iprodione, procymidone, vinclozolin;
nonaromatic 5-membered heterocyclic rings: famoxadon, fenamidon, flutianil, octhilinone, probenazole, S-allyl 5-amino-2-isopropyl-3-oxo-4-orthotolyl-2,3-dihydropyrazole-1-thiocarboxylate;
others: acibenzolar-S-methyl, amisulbrom, anilazin, blasticidin-S, captafol, captan, quinomethionate, dazomet, debacarb, diclomezine, difenzoquat, difenzoquat methylsulfate, fenoxanil, folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxypyrimidin-2-yl)-2-methyl-1H-benzimidazole, 5-chloro-7-(4-methylpiperidin-1-yl)-6-(2,4,6-trifluorophenyl)-[1,2,4]triazolo[1,5-a]pyrimidine, 5-ethyl-6-octyl-[1,2,4]triazolo[1,5-a]pyrimidin-7-ylamine;

E) Carbamates and Dithiocarbamates
thio- and dithiocarbamates: ferbam, mancozeb, maneb, metam, methasulphocarb, metiram, propineb, thiram, zineb, ziram;
carbamates: diethofencarb, benthiavalicarb, iprovalicarb, propamocarb, propamocarb hydrochloride, valiphenal, (4-fluorophenyl) N-(1-(1-(4-cyanophenyl)ethanesulfonyl)-but-2-yl)carbamate;

F) Other Fungicides
guanidines: dodine, dodine free base, guazatine, guazatine acetate, iminoctadine, iminoctadine triacetate, iminoctadine tris(albesilate);
antibiotics: kasugamycin, kasugamycin hydrochloride hydrate, polyoxins, streptomycin, validamycin A;
nitrophenyl derivatives: binapacryl, dicloran, dinobuton, dinocap, nitrothal-isopropyl, tecnazene;
organometallic compounds: fentin salts such as, for example, fentin acetate, fentin chloride, fentin hydroxide;
sulfurous heterocyclyl compounds: dithianon, isoprothiolane;
organophosphorus compounds: edifenphos, fosetyl, fosetyl-aluminum, iprobenfos, phosphorous acid and its salts, pyrazophos, tolclofos-methyl;
organochlorine compounds: chlorthalonil, dichlofluanid, dichlorphen, flusulfamide, hexachlorobenzene, pencycuron, pentachlorophenol and its salts, phthalide, quintozene, thiophanate-methyl, tolylfluanid, N-(4-chloro-2-nitrophenyl)-N-ethyl-4-methylbenzenesulfonamide;
inorganic active substances: phosphorous acid and its salts, Bordeaux mixture, copper salts such as, for example, copper acetate, copper hydroxide, copper oxychloride, basic copper sulfate, sulfur;
biological products for controlling fungi, plant strengthening products: *Bacillus subtilis* strain NRRL No. B-21661 (for example the products RHAPSODY®, SERENADE® MAX and SERENADE® ASO from AgraQuest, Inc., USA.), *Bacillus pumilus* strain NRRL No. B-30087 (for example SONATA® and BALLAD® Plus from AgraQuest, Inc., USA), *Ulocladium oudemansll* (for example BOTRY-ZEN from BotriZen Ltd., New Zealand), chitosan (for example ARMOUR-ZEN from BotriZen Ltd., New Zealand).
others: biphenyl, bronopol, cyflufenamid, cymoxanil, diphenylamine, metrafenon, mildiomycin, oxine-copper, prohexadione-calcium, spiroxamin, tolylfluanid, N-(cyclo-propylmethoxyimino-(6-difluoromethoxy-2,3-difluorophenyl)methyl)-2-phenyl-acetamide, N'-(4-(4-chloro-3-trifluoromethylphenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine, N'-(5-difluoromethyl-2-methyl-4-(3-trimethylsilanylpropoxy)phenyl)-N-ethyl-N-methylformamidine, N-methyl-(1,2,3,4-tetrahydronaphthalen-1-yl)-2-{1-[2-(5-methyl-3-trifluoromethylpyrazol-1-yl)acetyl]piperidin-4-yl}thiazole-4-carboxylate, N-methyl-(R)-1,2,3,4-tetrahydronaphthalen-1-yl 2-{1-[2-(5-methyl-3-trifluoromethylpyrazol-1-yl)acetyl]piperidin-4-yl}thiazole-4-carboxylate, 6-tert-butyl-8-fluoro-2,3-dimethylquinolin-4-ylacetate, 6-tert-butyl-8-fluoro-2,3-di-methylquinolin-4-yl methoxyacetate, N-methyl-2-{1-[2-(5-methyl-3-trifluoromethyl-1H-pyrazol-1-yl)acetyl]piperidin-4-yl}-N-[(1R)-1,2,3,4-tetrahydronaphthalen-1-yl]-4-thiazolecarboxamide;

G) Growth Regulators
abscisic acid, amidochlor, ancymidole, 6-benzylaminopurine, brassinolide, butralin, chlormequat (chlormequat chloride), choline chloride, cyclanilid, daminozide, dikegulac, dimethipin, 2,6-dimethylpuridine, ethephon, flumetralin, flurprimidol, fluthiacet, forchlorfenuron, gibberellic acid, inabenfid, indole-3-acetic acid, maleic hydrazide, mefluidid, mepiquat (mepiquat chloride), metconazole, naphthaleneacetic acid, N-6-benzyladenine, paclobutrazole, prohexadione (prohexadione-calcium), prohydrojasmone, thidiazuron, triapenthenol, tributylphosphorotrithioate, 2,3,5-triiodo-benzoic acid, trinexapac-ethyl and uniconazole;

H) Herbicides
acetamide: acetochlor, alachlor, butachlor, dimethachlor, dimethenamid, flufenacet, mefenacet, metolachlor, metazachlor, napropamid, naproanilid, pethoxamid, pretilachlor, propachlor, thenylchlor;

amino acid analogs: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

bipyridyls: diquat, paraquat;

carbamates and thiocarbamates: asulam, butylate, carbetamide, desmedipham, dimepiperat, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oyfluorfen;

hydroxybenzonitriles: bromoxynil, dichlobenil, ioxynil;

imidazolinones: imazamethabenz, imazamox, imazapic, imazapyr, imazaquin, imazethapyr;

phenoxyacetic acids: clomeprop, 2,4-dichlorophenoxyacetic acid (2,4-D), 2,4-DB, dichlorprop, MCPA, MCPA-thioethyl, MCPB, mecoprop;

pyrazines: chloridazon, flufenpyr-ethyl, fluthiacet, norflurazon, pyridate;

pyridines: aminopyralid, clopyralid, diflufenican, dithiopyr, fluridone, fluoroxypyr, picloram, picolinafen, thiazopyr;

sulfonylureas: amidosulfuron, azimsulfuron, bensulfuron, chlorimuron-ethyl, chlorsulfuron, cinosulfuron, cyclosulfamuron, ethoxysulfuron, flazasulfuron, fluceto-sulfuron, flupyrsulfuron, foramsulfuron, halosulfuron, imazosulfuron, iodosulfuron, mesosulfuron, metsulfuron-methyl, nicosulfuron, oxasulfuron, primisulfuron, pro-sulfuron, pyrazosulfuron, rimsulfuron, sulfometuron, sulfosulfuron, thifensulfuron, tris-sulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxypyrimidin-2-yl)urea;

triazines: ametryne, atrazine, cyanazine, dimethametryne, ethiozine, hexazinone, metamitron, metribuzine, prometryne, simazine, terbuthylazine, terbutryne, triaziflam;

ureas: chlortoluron, daimuron, diuron, fluometuron, isoproturon, linuron, methabenz-thiazuron, tebuthiuron;

other acetolactate synthase inhibitors: bispyribac-sodium, cloransulam-methyl, diclosulam, florasulam, flucarbazone, flumetsulam, metosulam, orthosulfamuron, penoxsulam, propoxycarbazone, pyribambenz-propyl, pyribenzoxim, pyriftalide, pyriminobac-methyl, pyrimisulfan, pyrithiobac, pyroxasulfon, pyroxsulam;

others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethyl, chlorthal, cinmethylin, clomazone, cumyluron, cyprosulfamid, dicamba, difenzoquat, diflufenzopyr, *Drechslera monoceras*, endothal, ethofumesate, etobenzanid, fentrazamide, flumiclorac-pentyl, flumioxazin, flupoxam, fluorochloridon, flurtamon, indanofan, isoxaben, isoxaflutol, lenacil, propanil, propyzamide, quinclorac, quinmerac, mesotrione, methylarsenic acid, naptalam, oxadiargyl, oxadiazone, oxaziclomefon, pentoxazone, pinoxaden, pyraclonil, pyraflufen-ethyl, pyrasulfotol, pyrazoxyfen, pyrazolynate, quinoclamin, saflufenacil, sulcotrione, sulfentrazone, terbacil, tefuryltrione, tembotrione, thiencarbazone, topramezone, 4-hydroxy-3-[2-(2-methoxyethoxymethyl)-6-trifluoromethylpyridin-3-carbonyl]bicyclo[3.2.1]oct-3-en-2-one, ethyl (3-[2-chloro-4-fluoro-5-(3-methyl-2,6-dioxo-4-trifluoromethyl-3,6-dihydro-2H-pyrimidin-1-yl)phenoxy]pyridin-2-yloxy)acetate, methyl 6-amino-5-chloro-2-cyclo-propylpyrimidine-4-carboxylate, 6-chloro-3-(2-cyclopropyl-6-methylphenoxy)-pyridazin-4-ol, 4-amino-3-chloro-6-(4-chlorophenyl)-5-fluoropyridin-2-carboxylic acid, methyl 4-amino-3-chloro-6-(4-chloro-2-fluoro-3-methoxyphenyl)pyridin-2-carboxylate and methyl 4-amino-3-chloro-6-(4-chloro-3-dimethylamino-2-fluorophenyl)pyridin-2-carboxylate;

I) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, taufluvalinate, tefluthrin, tetramethrin, tralomethrin, transfluthrin, profluthrin, dimefluthrin, insect growth inhibitors: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazin; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramate;

nicotine receptor agonists/antagonists: clothianidin, dinotefuran, imidacloprid, thiamethoxam, nitenpyram, acetamiprid, thiacloprid, 1-(2-chlorothiazol-5-ylmethyl)-2-nitrimino-3,5-dimethyl-[1,3,5]triazinane;

GABA antagonists: endosulfan, ethiprole, fipronil, vaniliprole, pyrafluprole, pyriprole, N-5-amino-1-(2,6-dichloro-4-methylphenyl)-4-sulfinamoyl-1H-pyrazole-3-thiocarboxamide;

macrocyclic lactones: abamectin, emamectin, milbemectin, lepimectin, spinosad, spinetoram;

mitochondrial electron transport chain inhibitor (METI) I acaricides: fenazaquin, pyridaben, tebufenpyrad, tolfenpyrad, flufenerim;

METI II and III substances: acequinocyl, fluacyprim, hydramethylnone;

decouplers: chlorfenapyr;

inhibitors of oxidative phosphorylation: cyhexatin, diafenthiuron, fenbutatin oxide, propargite;

insect ecdysis inhibitors: cryomazin;

'mixed function oxidase' inhibitors: piperonyl butoxide;

sodium channel blockers: indoxacarb, metaflumizon;

others: benclothiaz, bifenazate, cartap, flonicamid, pyridalyl, pymetrozin, sulfur, thiocyclam, flubendiamid, chlorantraniliprole, cyazypyr (HGW86); cyenopyrafen, flupyrazofos, cyflumetofen, amidoflumet, imicyafos, bistrifluoron and pyrifluquinazone.

Preferred pesticides comprise at least one pesticide with at least one H-acidic group (such as carboxylic acid group, phosphonic acid group, phosphinic acid group) or the anionic salts thereof (e.g., mono, di or tri salts). These anionic salts of the pesticides with an H-acidic group are also suitable as anionic pesticides in group A⁻. Preferred pesticides with an H-acidic group are herbicides with an H-acidic group. Examples of herbicides with an H-acidic group are amino acid analogs (such as glyphosate or glufosinate) or imidazolinones (such as imazamethabenz, imazamox, imazapic, imazapyr, imazaquin, imazethapyr).

Particularly preferred pesticides with an H-acidic group are glyphosate and glufosinate. In another preferred embodiment, pesticides with an H-acidic group are imidazolinones.

Especially preferably, the pesticide comprises a pesticide with an H-acidic group and a further pesticide. In another embodiment the pesticide comprises mixtures of at least two pesticides with an H-acidic group, and optionally further pesticides (such as at least one fungicide, herbicide, insecticide, and/or safener, with fungicides and/or herbicides being preferred).

In a further preferred embodiment, the pesticide comprises glyphosate (for example as the free acid, sodium salt, sesquisodium salt, potassium salt, dipotassium salt, ammonium salt, diammonium salt, dimethylammonium salt, trimesium salt or isopropyl-amine sale) or glufosinate (for example as the ammonium salt). With particular preference the pesticide comprises glyphosate (for example as the potassium salt, ammonium salt or isopropylamine salt). With particular preference the pesticide comprises glyphosate or glufosinate, and additionally a further herbicide. In another preferred embodiment the pesticide comprises glyphosate or glufosinate, and additionally a further pesticide (such as at least one fungicide, herbicide, insecticide and/or safener, with fungicides and/or herbicides being preferred).

The compositions according to the invention can furthermore also comprise adjuvants conventionally used for agrochemical formulations, the choice of the adjuvants depending on the specific use form, the type of formulation or the active substance. Examples of suitable adjuvants are solvents, solid carriers, surface-active substances (such as surfactants, solubilizers, protective colloids, wetters and tackifiers), organic and inorganic thickeners, bactericides, antifreeze agents, antifoams, optionally colorants and adhesives (for example for the treatment of seed) or conventional adjuvants for bait formulations (for example attractants, feedants, bittering substances).

Suitable solvents are water or organic solvents such as mineral oil fractions of medium to high boiling point such as kerosene and diesel oil, furthermore coal tar oils and oils of vegetable or animal origin, aliphatic, cyclic and aromatic hydrocarbons, for example paraffins, tetrahydronaphthalene, alkylated naphthalenes and their derivatives, alkylated benzenes and their derivatives, alcohols such as methanol, ethanol, propanol, butanol and cyclohexanol, glycols, ketones such as cyclohexanone, gamma-butyrolactone, dimethyl fatty acid amides, fatty acids and fatty acid esters, and strongly polar solvents, for example amines such as N-methylpyrrolidone. In principle, it is also possible to use solvent mixtures and mixtures of the abovementioned solvents and water.

Solid carriers are mineral earths such as silicas, silica gels, silicates, talc, kaolin, limestone, lime, chalk, bole, loess, clay, dolomite, diatomaceous earth, calcium and magnesium sulfate, magnesium oxide, ground synthetic materials, fertilizers such as ammonium sulfate, ammonium phosphate, ammonium nitrate, ureas and vegetable products such as cereal meal, tree bark meal, wood meal and nutshell meal, cellulose powders or other solid carriers.

Surface-active substances (adjuvants, wetters, tackifiers, dispersants or emulsifiers) which are suitable are the alkali metal, alkaline-earth metal, ammonium salts of aromatic sulfonic acids, for example of lignosulfonic acid (Borresperse® types, Borregaard, Norway), phenolsulfonic acid, naphthalenesulfonic acid (Morwet® types, Akzo Nobel, USA) and dibutylnaphthalenesulfonic acid (Nekal® types, BASF, Germany), and of fatty acids, alkyl- and alkylarylsulfonates, alkyl ether, lauryl ether and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin-sulfite liquors and proteins, denatured proteins, polysaccharides (for example methylcellulose), hydrophobe-modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone and their copolymers.

The composition according to the invention may comprise from 0.1 to 40% by weight, preferably from 1 to 30 and in particular from 2 to 20% by weight of surface-active substances, the amount of the alkoxylate (A) and (AQ) not being taken into consideration.

Suitable thickeners are compounds which impart to the formulation a modified flow behavior, i.e. high viscosity at rest and low viscosity in the agitated state. Examples are polysaccharides, proteins (such as casein or gelatins), synthetic polymers, or inorganic layered minerals. Such thickeners are commercially available, for example Xanthan Gum (Kelzan®, CP Kelco, USA), Rhodopol® 23 (Rhodia, France) or Veegum® (R.T. Vanderbilt, USA) or Attaclay® (Engelhard Corp., NJ, USA). The thickener content in the formulation depends on the efficacy of the thickener. The skilled worker will choose such a content that the desired viscosity of the formulation is obtained. The content will amount to from 0.01 to 10% by weight in most cases.

Bactericides may be added in order to stabilize the composition. Examples of bactericides are those based on dichlorophene and benzyl alcohol hemiformal and also isothiazolinone derivatives such as alkylisothiazolinones and benzoisothiazolinones (Acticide® MBS from Thor Chemie). Examples of suitable antifreeze agents are ethylene glycol, propylene glycol, urea and glycerol. Examples of antifoams are silicone emulsions (such as, for example, Silikon® SRE, Wacker, Germany or Rhodorsil®, Rhodia, France), long-chain alcohols, fatty acids, salts of fatty acids, organofluorine compounds and mixtures of these.

The composition according to the invention can preferably be present in the form of an agrochemical formulation. Examples of such formulations and their preparation are:
i) Water-soluble concentrates (SL, LS): 10 parts by weight of the active substances are dissolved using 90 parts by weight of water or a water-soluble solvent. Alternatively, wetters or other adjuvants are added. Upon dilution in water, the active substance dissolves. This gives a composition with an active substance content of 10% by weight.

ii) Dispersible concentrates (DC): 20 parts by weight of the active substances are dissolved in 70 parts by weight of cyclohexanone with addition of 10 parts by weight of a dispersant, for example polyvinylpyrrolidone. Upon dilution in water, a dispersion is obtained. The active substance content amounts to 20% by weight iii) Emulsifiable concentrates (EC): 15 parts by weight of the active substances are dissolved in 75 parts by weight of xylene with addition of calcium dodecylbenzene-sulfonate and castor oil ethoxylate (in each case 5 parts by weight). Upon dilution in water, an emulsion is obtained. The composition has an active substance content of 15% by weight.

iv) Emulsions (EW, EO, ES): 25 parts by weight of the active substances are dissolved in 35 parts by weight of xylene with addition of calcium dodecylbenzene-sulfonate and castor oil ethoxylate (in each case 5 parts by weight). Using an emulsifier (for example Ultra-Turrax), this mixture is placed into 30 parts by weight of water and made into a homogeneous emulsion. Upon dilution in water, an emulsion results. The composition has an active substance content of 25% by weight.

v) Suspensions (SC, OD, FS): 20 parts by weight of the active substances are comminuted with addition of 10 parts by weight of dispersants and wetters and 70 parts by weight of water or an organic solvent in a stirred-ball mill to give a finely divided active substance suspension. Upon dilution in water, a stable suspension of the active substance is obtained. The active substance content in the composition amounts to 20% by weight.

vi) Water-dispersible and water-soluble granules (WG, SG): 50 parts by weight of the active substances are ground finely with addition of 50 parts by weight of dispersants and wetters and formulated as water-dispersible or water-soluble granules by means of technical apparatuses (for example extrusion, spray tower, fluidized bed). Upon dilution in water, a stable dispersion or solution of the active substance is obtained. The composition has an active substance content of 50% by weight.

vii) Water-dispersible and water-soluble powders (WP, SP, SS, WS): 75 parts by weight of the active substances are ground in a rotor-stator mill with addition of 25 parts by weight of dispersants and wetters and also silica gel. Upon dilution in water, a stable dispersion or solution of the active substance is obtained. The active substance content of the composition amounts to 75% by weight.

viii) Gels (GF): in a ball mill, 20 parts by weight of the active substances, 10 parts by weight of dispersant, 1 part by weight of gelling agent and 70 parts by weight of water or an organic solvent are ground to give a fine suspension. Upon dilution with water, a stable suspension with an active substance content of 20% by weight is obtained.

ix) Dusts (DP, DS): 5 parts by weight of the active substances are ground finely and mixed intimately with 95 parts by weight of finely divided kaolin. This gives a dust with an active substance content of 5% by weight.

x) Granules (GR, FG, GG, MG): 0.5 part by weight of the active substances is ground finely and associated with 99.5 parts by weight of carriers. Conventional methods to this end are extrusion, spray-drying or the fluidized bed. This gives granules for direct application with an active substance content of 0.5% by weight.

xi) ULV solutions (UL): 10 parts by weight of the active substances are dissolved in 90 parts by weight of an organic solvent, for example xylene. This gives a composition to be applied directly with an active substance content of 10% by weight.

In general, the compositions comprise from 0.01 to 95% by weight, preferably from 0.1 to 90% by weight, of the pesticides.

The user will generally use the composition according to the invention for use in a premetering device, in a knapsack sprayer, in a spray tank or in a spraying aircraft. Here, the formulation is brought to the desired use concentration with water and/or buffer, optionally with addition of further auxiliaries, whereby the ready-to-use spray mixture (known as a tank mix) is obtained. Usually, 50 to 500 liters of the ready-to-use spray mixture are applied per hectare of utilizable agricultural area, preferably from 100 to 400 liters. In specific segments the amounts may also be above (e.g., fruit growing) or below (e.g., aircraft application) these amounts. The active substance concentrations in the ready-to-use preparations may be varied within substantial ranges. In general, they are between 0.0001 and 10%, preferably between 0.01 and 1%.

Oils of various types, wetters, drift reduction agents, stickers, spreaders, adjuvants, fertilizers, plant-strengthening products, trace elements, herbicides, bactericides, fungicides and/or pesticides may be added to the active substances or to the preparations comprising them, optionally also to the tank mix, immediately prior to use. These products can be admixed to the compositions according to the invention in the weight ratio 1:100 to 100:1, preferably 1:10 to 10:1. Adjuvants which are suitable within this context are in particular: organic-modified polysiloxanes, for example Break Thru S 240®; alcohol alkoxylates, for example Atplus® 245, Atplus® MBA 1303, Plurafac® LF 300 and Lutensol® ON 30; EO/PO block polymers, for example Pluronic® RPE 2035 and Genapol® B; alcohol ethoxylates, for example Lutensol® XP 80; and sodium dioctyl sulfosuccinate, for example Leophen® RA.

Depending on the nature of the desired effect, the application rates of the active substance when used in plant protection are between 0.001 and 2.0 kg of active substance per ha, preferably between 0.005 and 2 kg per ha, especially preferably between 0.05 and 0.9 kg per ha, in particular between 0.1 and 0.75 kg per ha.

The present invention furthermore relates to a method of controlling phytopathogenic fungi and/or undesired vegetation and/or undesired insect or mite attack and/or for regulating the growth of plants, wherein the composition according to the invention is allowed to act on the respective pests, their environment or the plants to be protected from the respective pest, on the soil and/or on undesirable plants and/or the crop plants and/or their environment.

Examples of suitable crop plants are cereals, for example wheat, rye, barley, triticale, oats or rice; beet, for example sugar or fodder beet; pome fruit, stone fruit and soft fruit, for example apples, pears, plums, peaches, almonds, cherries, strawberries, raspberries, currants or gooseberries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capsicums; plants of the laurel family, for example avocados, cinnamon or camphor; energy crops and industrial feedstock crops, for example maize, soybeans, wheat, oilseed rape, sugar cane or oil palm; maize; tobacco; nuts; coffee; tea;

bananas; wine (dessert grapes and grapes for vinification); hops; grass, for example turf; sweetleaf (*Stevia rebaudania*); rubber plants and forest plants, for example flowers, shrubs, deciduous trees and coniferous trees, and propagation material, for example seeds, and harvested produce of these plants.

The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding polymers such as, for example, prenylated, acetylated or farnesylated residues or PEG residues.

Examples which may be mentioned are plants which, as the result of plant-breeding and recombinant measures, have acquired a tolerance for certain classes of herbicides, such as hydroxyphenylpyruvate dioxygenase (HPPD) inhibitors, acetolactate synthase (ALS) inhibitors such as, for example, sulfonylureas (EP-A 257 993, U.S. Pat. No. 5,013,659) or imidazolinones (for example U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073), enolpyruvylshikimate 3-phosphate synthase (EPSPS) inhibitors such as, for example, glyphosate (see, for example, WO 92/00377), glutamine synthetase (GS) inhibitors such as, for example, glufosinate (see, for example, EP-A 242 236, EP-A 242 246) or oxynil herbicides (see, for example, U.S. Pat. No. 5,559,024). For example, breeding and mutagenesis have given rise to Clearfield® oilseed rape (BASF SE, Germany), which features tolerance for imidazolinones, for example imazamox. With the aid of recombinant methods, crop plants such as soybeans, cotton, maize, beet and oilseed rape have been generated which are resistant to glyphosate or glufosinate, and these are available by the brand names RoundupReady® (glyphosate-resistant, Monsanto, U.S.A.) and Liberty Link® (glufosinate-resistant, Bayer CropScience, Germany).

Also comprised are plants which, with the aid of recombinant measures, produce one or more toxins, for example those from the bacterial strain *Bacillus*. Toxins which are produced by such genetically modified plants comprise, for example, insecticidal proteins of *Bacillus* spp., in particular from *B. thuringiensis*, such as the endotoxins Cry1Ab, Cry1Ac, Cry1F, Cry1Fa2, Cry2Ab, Cry3A, Cry3Bb1, Cry9c, Cry34Ab1 or Cry35Ab1; or vegetable insecticidal proteins (VIPs), for example VIP1, VIP2, VIP3, or VIP3A; insecticidal proteins from nematode-colonizing bacteria, for example *Photorhabdus* spp. or *Xenorhabdus* spp.; toxins from animal organisms, for example wasp, spider or scorpion toxins; fungal toxins, for example from *Streptomycetes*; plant lectins, for example from pea or barley; agglutinins; proteinase inhibitors, for example trypsin inhibitors, serine protease inhibitors, patatin, cystatin or papain inhibitors; ribosome-inactivating proteins (RIPs), for example ricin, maize RIP, abrin, luffin, saporin or bryodin; steroid-metabolizing enzymes, for example 3-hydroxysteroid oxidase, ecdysteroid IDP glycosyl transferase, cholesterol oxidase, ecdysone inhibitors or HMG CoA-reductase; ion channel blockers, for example inhibitors of sodium or calcium channels; juvenile hormone esterase; receptors for the diuretic hormone (helicokinin receptors); stilbene synthase, bibenzyl synthase, chitinases and glucanases. These toxins can also be produced, in the plants, in the form of pretoxins, hybrid proteins, truncated or otherwise modified proteins. Hybrid proteins are distinguished by a novel combination of different protein domains (see, for example, WO 2002/015701). Further examples of such toxins or genetically modified plants which produce these toxins are disclosed in EP-A 374 753, WO 93/07278, WO 95/34656, EP-A 427 529, EP-A 451 878, WO 03/18810 and WO 03/52073. The methods for generating these genetically modified plants are known to the skilled worker and explained, for example, in the abovementioned publications. A large number of the abovementioned toxins impart to the plants which produce them a tolerance for pests from all taxonomic classes of the arthropods, in particular beetles (Coeleropta), dipterans (Diptera) and lepidopterans (*Lepidoptera*) and nematodes (Nematoda). Genetically modified plants which produce one or more genes which code for insecticidal toxins are described for example in the abovementioned publications and are in some cases commercially available such as, for example, YieldGard® (maize varieties which produce the toxin Cry1Ab), YieldGard® Plus (maize varieties which produce the toxins Cry1Ab and Cry3Bb1), Starlink® (maize varieties which produce the toxin Cry9c), Herculex® RW (maize varieties which produce the toxins Cry34Ab1, Cry35Ab1 and the enzyme phosphinothricin N-acetyltransferase [PAT]); NuCOTN® 33B (cotton varieties which produce the toxin Cry1Ac), Bollgard® I (cotton varieties which produce the toxin Cry1Ac), Bollgard® II (cotton varieties which produce the toxins Cry1Ac and Cry2Ab2); VIPCOT® (cotton varieties which produce a VIP toxin); NewLeaf® (potato varieties which produce the toxin Cry3A); Bt-Xtra®, NatureGard®, KnockOut®, BiteGard®, Protecta®, Bt11 (for example Agrisure® CB) and Bt176 from Syngenta Seeds SAS, France, (maize varieties which produce the toxin Cry1Ab and the PAT enzyme), MIR604 from Syngenta Seeds SAS, France (maize varieties which produce a modified version of the toxin Cry3A, see in this context WO 03/018810), MON 863 from Monsanto Europe S.A., Belgium (maize varieties which produce the toxin Cry3Bb1), IPC 531 from Monsanto Europe S.A., Belgium (cotton varieties which produce a modified version of the toxin Cry1Ac) and 1507 from Pioneer Overseas Corporation, Belgium (maize varieties which produce the toxin Cry1F and the PAT enzyme).

Also comprised are plants which, with the aid of recombinant measures, produce one or more proteins which bring about an increased resistance to, or ability to withstand, bacterial, viral or fungal pathogens such as, for example, so-called pathogenesis-related proteins (PR proteins, see EP-A 0 392 225), resistance proteins (for example potato varieties which produce two resistance genes against *Phytophthora infestans* from the Mexican wild potato *Solanum bulbocastanum*) or T4 lysozyme (for example potato varieties which, as the result of the production of this protein, are resistant to bacteria such as *Erwinia amylvora*).

Also comprised are plants whose productivity has been improved with the aid of recombinant methods, for example by increasing the yield potential (for example biomass, grain yield, starch content, oil content or protein content), the tolerance for drought, salt or other limiting environmental factors, or the resistance to pests and fungal, bacterial and viral pathogens.

Also comprised are plants whose constituents, in particular for improving human or animal nutrition, have been modified with the aid of recombinant methods, for example by oil plants producing health-promoting long-chain omega-3-fatty acids or monounsaturated omega-9-fatty acids (for example Nexera® oilseed rape, DOW Agro Sciences, Canada).

The present invention also relates to seed (such as seeds or other plant propagation materials) comprising the composition according to the invention. Plant propagation materials can be treated preventively with the composition according to the invention at the point of or even before sowing or at the point of or even before transplanting. For the treatment of seed, one will generally use water-soluble concentrates (LS), suspensions (FS), dusts (DS), water-dispersible and water-soluble powders (WS, SS), emulsions (ES), emulsifiable concentrates (EC) and gels (GF). These compositions can be applied to the propagation materials, in particular seed, in undiluted form or, preferably, in diluted form. Here, the composition in question can be diluted 2- to 10-fold, so that from 0.01 to 60% by weight, preferably from 0.1 to 40% by weight, of active substance is present in the compositions used for the seed dressing. The application may be effected before or during sowing. The treatment of plant propagation material, in particular the treatment of seed, is known to the skilled worker and carried out by dusting, coating, pelleting, dipping or soaking the plant propagation material, the treatment preferably being carried out by pelleting, coating and dusting or by in-furrow treatment so that, for example, untimely early germination of the seed is prevented. It is preferred to use suspensions for the treatment of seed. Usually, such compositions comprise from 1 to 800 g/l of active substance, from 1 to 200 g/l of surfactants, from 0 to 200 g/l of antifreeze agents, from 0 to 400 g/l of binders, from 0 to 200 g/l of colorants and solvent, preferably water.

The present invention furthermore relates to an alkoxylate, wherein the alkoxylate is an amine alkoxylate (A)

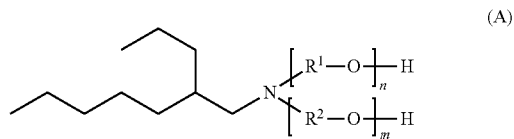

(A)

or a quaternized derivative (AQ)

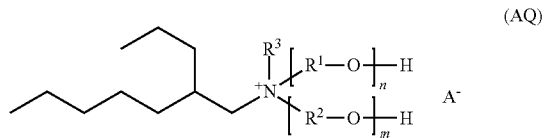

(AQ)

of the amine alkoxylate (A), where $R^1$, $R^2$, and $R^5$ independently of one another are ethylene, propylene, butylene or a mixture of these, $R^3$ is an H, —OH, —OR$^4$, $C_1$-$C_6$-alkyl or an oxygen anion, $R^4$ is a $C_1$-$C_6$-alkyl, $C_2$-$C_6$-alkenyl or $C_2$-$C_6$-alkynyl, $R^6$ is an H, $C_1$-$C_6$-alkyl, $C_2$-$C_6$-alkenyl, $C_2$-$C_6$-alkynyl, —SO$_3$R$^a$, —P(O)OR$^b$OR$^c$, —CH$_2$CO$_2$R$^d$, or —C(O)R$^e$, $R^a$ and $R^d$ independently of one another are an H, inorganic or organic cations, $R^1$, and $R^c$ independently of one another are an H, inorganic or organic cations, $C_1$-$C_6$-alkyl, $C_2$-$C_6$-alkenyl or $C_2$-$C_6$-alkynyl, $R^e$ is $C_1$-$C_{22}$-alkyl, $C_2$-$C_{22}$-alkenyl, $C_2$-$C_{22}$-alkynyl, $C_6$-$C_{22}$-aryl or $C_7$-$C_{22}$-alkylaryl, n, m and p independently of one another have a value of from 1 to 30, A⁻ is an agriculturally acceptable anion, or, if $R^3$ is an oxygen anion, A⁻ is absent. Preferred parameters are as described above.

In one embodiment the alkoxylate is a quaternized derivative (AQ) of the amine alkoxylate (A). In a preferred embodiment, the alkoxylate is an amine alkoxylate (A).

In a further preferred embodiment, the alkoxylate is a quaternized derivative (AQ) of the amine alkoxylate (A). Here, A⁻ is preferably a halide (such as chloride or bromide), phosphate, sulfate or an anionic pesticide. A⁻ is especially preferably an anionic pesticide, such as glyphosate anion or glufosinate anion.

The present invention furthermore relates to processes for the preparation of the amine alkoxylate (A) or a quaternized derivative (AQ) of the amine alkoxylate (A), comprising the alkoxylation of 2-propylheptylamine with ethylene oxide, propylene oxide, butylene oxide or a mixture of these. The preparation of 2-propylheptylamine is generally known, for example by reacting ammonia with 2-propylheptanol as described in U.S. Pat. No. 5,808,158.

The alkoxylation can be catalyzed by strong bases, such as alkali metal hydroxides and alkaline earth metal hydroxides, Brönsted acids or Lewis acids, such as AlCl$_3$, BF$_3$. Catalysts such as hydrotalcite or DMC may be used for alcohol alkoxylates with a narrow distribution. The alkoxylation is preferably carried out at temperatures in the range of approximately 80 to 250° C., preferably approximately 100 to 220° C. The pressure is preferably between ambient pressure and 600 bar. If desired, the alkylene oxide may comprise an admixture of inert gas, for example of approximately 5 to 60%.

The quaternized derivative (AQ) of the amine alkoxylate (A) can be prepared in a further reaction step by quaternizing the amine alkoxylate (A). To introduce the radical $R^3$ into the amine alkoxylate (A), the latter may be reacted for example with an alkylation reagent such as methyl chloride, dimethyl sulfate or butyl chloride. To introduce the one oxygen anion into the amine alkoxylate (A), the latter may be oxidized, for example by reacting the amino group with hydrogen peroxide, peracids (such as meta-chloroperbenzoic acid or peracetic acid) or peroxymonosulfuric acid.

The quaternized derivatives (AQ) where $R^3$=H can be prepared by simple protonation of starting compounds of the structure (A). The quaternized derivatives (AQ) where $R^3$=OH can be prepared by simple protonation of starting compounds (AQ) where $R^3$=oxygen anion. Acids which are suitable for the protonation are organic acids (for example $C_1$- to $C_{20}$-carboxylic acids, in particular benzoic acid) or inorganic acids (for example hydrochloric acid, phosphoric acid or sulfuric acid). Others which are likewise suitable are H-acidic pesticides such as, for example, glyphosate-acid or glyphosate-monosalts. The protonation can be carried out in a separate synthesis, so that the quaternized derivative (AQ) can be isolated. It is also possible to carry out the protonation by mixing the starting compounds with one or more acids in the composition or in the spray mixture.

The present invention also relates to the use of the amine alkoxylate (A) or of a quaternized derivative (AQ) of the amine alkoxylate (A) as described above as auxiliary in pesticide-comprising spray mixtures. The auxiliary is preferably an activity-enhancing auxiliary. Such activity-enhancing auxiliaries are also referred to as adjuvants. They enhance or accelerate the activity of pesticides in comparison with the activity of the pesticide in the absence of the adjuvant.

The advantages of the invention are high stability of the formulation and of the spray mixture, little wind-caused drift in the case of spray applications, good adhesion of the formulation on the surface of the treated plants, increased solubility of the pesticides in the formulation, increased permeation of the pesticides into the plant and, as a result, more rapid and enhanced activity. An important advantage is the low toxicity of the novel alkoxylates, in particular the low aquatic toxicity. Another advantage is the low harmful effect against crop plants, i.e., low phytotoxic effects. A further advantage is the simple handling of these alkoxides since, for example, no gelling takes place upon their incorporation into formulations.

The examples which follow illustrate the invention without imposing any limitation.

EXAMPLES

Example 1

Synthesis of 2-propylheptylamine (2-PHamine)

2-Propylheptanol (commercially available from BASF SE or Evonik) and an alcohol amination catalyst (described in EP 696 572 A1; 8% by weight based on 2-propyl-heptanol) were introduced in the autoclave, and the system was flushed with nitrogen and hydrogen. Then ammonia was injected in a molar ratio of ammonia to alcohol of 17:1 and the mixture was heated with stirring. After a reaction time of ten hours at 210° C. and an $H_2$ pressure of 240 bar, the 2-propylheptylamine was filtered off and freed from water on a rotary evaporator.

Example 2

Alkoxylation of 2-propylheptylamine

A) Preparation of 2-PHamine-7 EO

First of all 628 g (4 mol) of 2-propylheptylamine from Example 1 were admixed with 19.6 g of water. Then, after flushing with nitrogen, at 100° C., 352 g (8 mol) of ethylene oxide (EO) were metered in. Subsequently, at 80° C., this batch was dewatered under reduced pressure. This gave a yield of 988 g (=99% of theory) with an OH number of 468 mg KOH/g (458 mg KOH/g theory) and an amine number of 229 mg KOH/g (229 mg KOH/g theory).

In a second step, 269.5 g (1.1 mol) of this precursor product were admixed with 2.0 g of 50% strength KOH, and dewatering took place at 90° C. under reduced pressure. After flushing with nitrogen, at 120° C., 242 g (=5.5 mol) of ethylene oxide were metered in. The product was adjusted to a pH (5% in water) of 9.9 with a few drops of acetic acid. This gave a yield of 512 g (100% of theory) of a yellowish liquid of low viscosity (OH number: 279.1 mg KOH/g (241 mg KOH/g theory); amine number: 120 mg KOH/g (121 mg KOH/g theory), water content <0.5% by weight).

B) Preparation of 2-PHamine-10 EO

First of all, 1280 g (8.15 mol) of 2-propylheptylamine from Example 1 were admixed with 40 g of water. Then, after flushing with nitrogen, at 100° C., 717 g (16.3 mol) of ethylene oxide were metered in (2 bar, 16 h). Subsequently, at 90° C., remaining traces of ethylene oxide were removed under reduced pressure. This gave a quantitative yield with an amine number of 229 mg KOH/g.

In the second step, 821.5 g (3.35 mol) of this precursor product were admixed with 8.0 g of 50% strength KOH and dewatering was carried out at 90° C. under reduced pressure. After flushing with nitrogen, at 120° C., 1179 g (=26.8 mol) of ethylene oxide were metered in (1.5 bar, 12 h). This gave a quantitative yield of a yellowish liquid of low viscosity.

C) to F) Preparation of 2-PHamine-5 EO, 2-PHamine-8.5 EO, 2-PHamine-15 EO, 2-PHamine-20 EO The ethoxylation of 2-propylheptylamine from Example 1 was carried out in accordance with Examples 2A and 2B. In this way it was possible in quantitative yield to synthesize 2-PHamine-5 EO, 2-PHamine-8.5 EO, 2-PHamine-15 EO and 2-PHamine-20 EO. Here, the codes "–5 EO", "–8.5 EO", etc., indicate the molar excess of ethylene oxide relative to 2-propylheptylamine.

G) Preparation of 2-PHamine-ethoxylate-propoxylate

General preparation instructions: 2-propylheptylamine (1 mol eq.; from Example 1) was admixed in the reactor with water (2% by weight, based on the total batch). Then, after flushing with nitrogen and adjustment of the pressure to 1.5 bar, at 100° C.-130° C., ethylene oxide (2 mol eq.) was metered in. This was followed by dewatering at 80° C. under reduced pressure. The yield is determined, and also the OH number and amine number, in order to determine the quality of the precursor product.

In the second step, this precursor product (1 mol eq.) was admixed with 50% strength KOH (0.2% by weight, based on the total batch) and dewatering was carried out at 90° C. under reduced pressure. After flushing with nitrogen, the pressure is adjusted to 1.5 bar and, at 120° C.-140° C., alkylene oxide (x mol eq. of ethylene oxide or propylene oxide or a mixture of propylene oxide or ethylene oxide) is metered in. The reaction mixture was stirred at this temperature until the pressure was constant.

Either the product was discharged and adjusted with glacial acetic acid to a pH of 9.9 (5% in water), or at the same temperature (120-140° C.) propylene oxide (y mol eq.) is metered in. The reaction mixture is stirred at this temperature until the pressure is constant. The product is isolated and adjusted with glacial acetic acid to a pH of 9.9 (5% in water).

The alkoxylation of 2-propylheptylamine to give 2-PHamine-5 EO-15 PO was carried out in accordance with the general preparation instructions. In the first step, reaction took place with a 2-molar excess of ethylene oxide, and in the second step the remaining ethylene oxide and propylene oxide were added. This gave 2-PHamine-5 EO-15 PO in quantitative yield.

H to Q) Preparation of 2-PHamine-propoxylate-ethoxylate

General preparation instructions: 2-propylheptylamine (1 mol eq.) was admixed in the reactor with water (2% by weight, based on the total batch). Then, after flushing with nitrogen and adjustment of the pressure to 1.5 bar, at 100° C.-130° C., propylene oxide (2 mol eq.) was metered in. This was followed by dewatering at 80° C. under reduced pressure. The yield was determined, and also the OH number and amine number, in order to determine the quality of the precursor product.

In the second step, this precursor product (1 mol eq.) was admixed with 50% strength KOH (0.2% by weight, based on the total batch) and dewatering was carried out at 90° C. under reduced pressure. After flushing with nitrogen, the pressure is adjusted to 1.5 bar and, at 120° C.-140° C., alkylene oxide (x mol eq. of ethylene oxide or propylene oxide or a mixture of propylene oxide or ethylene oxide) is metered in. The reaction mixture is stirred at this temperature until the pressure is constant.

Either the product was discharged and adjusted with glacial acetic acid to a pH of 9.9 (5% in water), or at the same temperature (120-140° C.) propylene oxide (y mol eq.) was metered in. The reaction mixture was stirred at this temperature until the pressure was constant. The product was isolated and adjusted with glacial acetic acid to a pH of 9.9 (5% in water).

In accordance with these instructions, the following alkoxylates were prepared, each with a quantitative yield:
I) 2-PHamine-2 PO-5 EO
J) 2-PHamine-2 PO-10 EO
K) 2-PHamine-2 PO-15 EO
L) 2-PHamine-4 PO-5 EO
M) 2-PHamine-4 PO-10 EO
N) 2-PHamine-4 PO-15 EO
O) 2-PHamine-6 PO-5 EO
P) 2-PHamine-6 PO-10 EO
Q) 2-PHamine-6 PO-15 EO Example 3

Glyphosate SL Formulation Against *Brachiarea multica*

In a field trial, seven experimental areas of in each case six square meters were subjected to treatment against the weed *Brachiarea multica*, in each case in two replications (i.e. two plots of in each case 3 m$^2$). To this end, in each case 1.0 l of spray solution (see table 1) was sprayed per plot using a manual sprayer. 1.0 l of the spray solution contained 7.5 ml of an aqueous formulation of dissolved glyphosate-isopropyl-ammonium salt. To prepare this formulation, 100 ml of amine alkoxylate of example 2 were previously made up to 1.0 l with 46% strength glyphosate-isopropylammonium salt solution. Two, five and seven days after the application, the destruction of the weed was estimated visually in percent. Rain fell repeatedly in the days between application and assessment.

For comparison purposes, a glyphosate formulation as above, but without amine alkoxylate, was prepared, and a commercial glyphosate formulation (Roundup®, Monsanto) which comprised 41.5% by weight of glyphosate-isopropylammonium salt and 15.5% by weight of ethoxylated tallow fatty amine with approximately 15 mol of ethylene oxide per amine group ("tallow fatty amine—15 EO") was also used.

TABLE 1

| | Proportion [%] of weed destroyed | | |
|---|---|---|---|
| Amine alkoxylate | 2 days | 5 days | 7 days |
| —[a] | 15 | 35 | 55 |
| Tallow fatty amine--15 EO[a] | 40 | 70 | 75 |
| 2-Ethylhexylamine-7 EO[a] | 25 | 60 | 77.5 |
| Isotridecylamine-9 EO[a] | 20 | 40 | 62 |
| 2-PHamine-7 EO (from Example 2) | 40 | 87.5 | 90 |

[a]Comparative experiment, not inventive.

The data in table 1 demonstrated that the 2-propylheptylamine ethoxylate according to the invention ("2-PHamine-7 EO") enhances and accelerates the activity of glyphosate. Also, the formulation was rainfast. At temperatures of from 5 to +55° C., the formulation was storage-stable for at least two weeks.

Upon addition of 2-PHamine-7 EO at 20° C. to the glyphosate solution, there was, advantageously, no gelling observed, as was usually the case when tallow fatty amine-15 EO was added.

Example 4

Water Toxicity

2-PHamine-7 EO (from Example 2): EC50 60 mg/l (48 h) on *Daphnia magna*, determined according to OECD Guideline 202 part 1.

2-PHamine-10 EO (from Example 2): fish toxicity LC50>100 mg/l (96 h), *Brachydanio rerio*, determined according to OECD 203; ISO 7346; 84/449/EEC, C.1.; EC50 (72 h)>100 mg/l, algae, determined according to OECD Guideline 201.

Lutensol® FA15 T (tallow fatty amine ethoxylate with 15 EO): EC50 2.6 mg/l (48 h) on *Daphnia magna*, determined according to OECD Guideline 202 part 1; fish toxicity LC50 1-10 mg/l (96 h), *Leuciscus idus* (safety data sheet of Mar. 8, 2006 from BASF SE).

Lutensol® FA 12 (oleylamine ethoxylate with 12 EO): EC50 0.1-1 mg/l (48 h) on *Daphnia magna*, fish toxicity LC50 1-10 mg/l (96 h), *Leuciscus idus* (safety data sheet of Aug. 18, 2006 from BASF SE).

Example 5

Glyphosate SL Formulation on Oilseed Rape

For the greenhouse tests, winter oilseed rape (cultivar Remy) was sown or potted in loamy sandy soil to a depth of 1-2 cm. When the plants had reached a growth height of 10 to 25 cm (i.e., around 10 to 21 days after sowing), the spray mixtures were applied to the plants in a spraying cabin.

A concentrated formulation comprising glyphosate isopropylammonium in solution in water and amine alkoxylate from Example 2 was diluted with deionized water and applied at a water application rate of 375 l/ha (140 g of glyphosate/ha and 300 g of amine alkoxylate/ha). The temperatures in the experimental period, which lasted for 3 to 4 weeks, were between 18-35° C. During this time, the experimental plants received optimum watering, with nutrients being supplied via the water used for watering.

The herbicidal activity was evaluated by awarding scores to the treated plants in comparison to the untreated control plants (Table 2). The evaluation scale ranges from 0% to 100% activity. 100% activity means the complete death at least of those parts of the plant that are above ground. Conversely, 0% activity means that there were no differences between treated and untreated plants. The results in Table 2 demonstrate the increased activity of the active substance as a result of addition of the amine alkoxylate.

TABLE 2

| Amine alkoxylate | Activity [%] after 14 days | Activity [%] after 21 days |
|---|---|---|
| —[a] | 51 | 69 |
| 2-PHamine-5 EO | 59 | 74 |
| 2-PHamine-7 EO | 75 | 86 |
| 2-PHamine-10 EO | 74 | 86 |
| 2-PHamine-15 EO | 63 | 74 |
| 2-PHamine-20 EO | 63 | 74 |
| 2-PHamine-5 EO-15 PO | 63 | 74 |
| N-Methyl-2-PHamine-7 EO[a], [b] | 56 | 65 |

[a]Comparative experiment, not inventive.
[b]Prepared in analogy to WO 2009/004044, by addition of methylamine to the corresponding enone, which was then ethoxylated in the same way as in Example 2A. The neutral N-methylamine (not quaternized) obtained in this way had an amine number of 117.8 mg KOH/g).

Example 6

Glyphosate SL Formulation on Wheat, Soybean or Maize

The experiments were carried out as in Example 5, on winter wheat (cultivar Cubus), soybean (cultivar Oxford), and maize (cultivar Amadeo). The application rate was 280 g of glyphosate/ha and 300 g of amine alkoxylate/ha. The results in Table 3 demonstrate the increased activity of the active substance as a result of addition of the amine alkoxylate.

TABLE 3

| | Activity [%] after 21 days | | |
|---|---|---|---|
| Amine alkoxylate | Winter wheat | Soybean | Maize |
| —[a] | 73 | 38 | 54 |
| 2-PHamine-8.5 EO | 96 | 93 | 89 |
| 2-Ethylhexylamine-7 EO[a] | 84 | 51 | 71 |

[a]Comparative experiment, not inventive.

Example 7

Glyphosate SL Formulation on Oilseed Rape

The experiments were carried out as in Example 5, on winter oilseed rape (cultivar Remy). The application rate was 140 g of glyphosate/ha and 300 g of amine alkoxylate/ha. The results in Table 4 demonstrate the increased activity of the active substance as a result of addition of the amine alkoxylate.

TABLE 4

| Amine alkoxylate | Activity [%] after 14 days | Activity [%] after 21 days |
|---|---|---|
| —[a] | 51 | 69 |
| 2-PHamine-2 PO-5 EO | 94 | 97 |
| 2-PHamine-2 PO-10 EO | 92 | 91 |
| 2-PHamine-2 PO-15 EO | 97 | 98 |
| 2-PHamine-4 PO-5 EO | 86 | 86 |
| 2-PHamine-4 PO-10 EO | 92 | 91 |
| 2-PHamine-4 PO-15 EO | 94 | 93 |
| 2-PHamine-6 PO-5 EO | 83 | 80 |
| 2-PHamine-6 PO-10 EO | 86 | 84 |
| 2-PHamine-6 PO-15 EO | 91 | 86 |

[a]Comparative experiment, not inventive.

Example 8

Imazamox SL Formulation on *Ambrosia* and *Chenopodium*

The experiments were carried out as in Example 5, on *Ambrosia artemisiifolia* (AMBEL) and *Chenopodium album* (CHEAL) and scored after 14 days. The spray mixture was prepared starting from an aqueous SL formulation containing 120 g/l imazamox ammonium salt and 1,2-propylene glycol. The application rate was 10 g of imazamox/ha and 400 g of amine alkoxylate/ha. The results are summarized in Table 5. For comparison, a tallow fatty amine ethoxylate with 12 ethylene oxide units was used (liquid, approximately 100% content, molar mass approximately 730 g/mol (calculated from OH number), available commercially as Lutensol® FA12K from BASF SE).

TABLE 5

| Amine alkoxylate | Activity [%] AMBEL | Activity [%] CHEAL |
|---|---|---|
| Lutensol ® FA12K[a] | 80 | 90 |
| 2-PHamine-5 EO | 80 | 93 |
| 2-PHamine-7 EO | 80 | 93 |
| 2-PHamine-10 EO | 83 | 90 |
| 2-PHamine-15 EO | 80 | 93 |
| 2-PHamine-20 EO | 85 | 93 |

[a]Comparative experiment, not inventive.

Example 9

Imazaquin, Chlormequat Chloride and Choline Chloride SL Formulation for Growth Regulation in Wheat The experiments were carried out as in Example 5, on wheat. The height of the stalks was measured 7, 14 and 21 days after application. The spray mixture was prepared starting from an aqueous SL formulation containing 0.8 g/l imazaquin, 368 g/l chlormequat chloride, 28 g/l choline chloride, and 80 g/l amine alkoxylate from Example 2C (2-PHamine-10 EO). The application rate was 1500 g/ha, 1000 g/ha or 500 g/ha of chlormequat chloride. The results are summarized in Table 6.

TABLE 6

| | Height of the wheat stalks [cm] 7, 14 and 21 days after application | | |
|---|---|---|---|
| Application rate of chlormequat chloride | 7 days | 14 days | 21 days |
| —[a] | 30.1 | 32.5 | 39.3 |
| 1500 g/ha | 25.1 | 25.1 | 26.4 |
| 1000 g/ha | 25.8 | 27.1 | 27.0 |
| 500 g/ha | 22.3 | 27.4 | 26.9 |

[a]Untreated wheat, comparative experiment, not inventive.

Example 10

Rain Resistance

Four maize plants and four winter wheat plants were each treated with 280 g/ha of glyphosate isopropylammonium salt and 300 g/ha of amine alkoxylate. After 1.5 or 3 h following this treatment, the plants were irrigated for 20 minutes with 100 l of water, at a pressure of 3.33 bar and a rate of 2.8 m/s. The plants were then placed in a greenhouse and rated as in Example 5 after 14 and 21 days. For comparison, Genamine® T150 was used ($C_{16/18}$-amine ethoxylate with 15 EO units, available commercially from Clariant).

Table 7 shows that the irrigation detaches the glyphosate less strongly from the plant, and so the activity remains high even after irrigation.

TABLE 7

| | Activity [%] after 21 days | | |
|---|---|---|---|
| Amine alkoxylate | | No irrigation | Irrigation 3 h after application |
| No application[a] | Maize | 0 | — |
| Genamine ® T 150[a] | Maize | 98 | 53 |

TABLE 7-continued

| | Activity [%] after 21 days | |
|---|---|---|
| Amine alkoxylate | | No irrigation | Irrigation 3 h after application |
| 2-PHamine-2 10 EO | Maize | 98 | 71 |
| No application[a] | Wheat | 0 | — |
| Genamine ® T 150[a] | Wheat | 100 | 94 |
| 2-PHamine-2 10 EO | Wheat | 100 | 97 |

[a]Comparative experiment, not inventive.

Example 11

Water-Soluble Granules SG

Glyphosate monoammonium salt (80.75 g) was mixed thoroughly with sodium sulfite (0.5 g) in a coffee grinder. The mixture was subsequently pasted up with a solution of 18.7 g of 2-PHamine-15 EO (from Example 2) and 4 g of water and extruded (benchtop, 0.8 mm perforated plate). The extrudate was subsequently dried and comminuted in order to give an extremely homogeneous granule size (average length approximately 1 mm). The water-soluble glyphosate granules (SG) obtained in this way were physically and chemically stable. From these granules it was possible, by dissolving them in water, to prepare spray mixtures (e.g., 2% strength) in a simple way, which were of high quality and stability.

We claim:

1. A composition comprising an alkoxylate, wherein the alkoxylate is an amine alkoxylate (A)

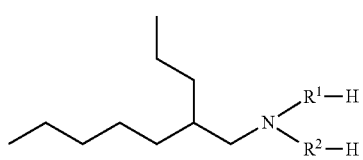

(A)

or a quaternized derivative (AQ)

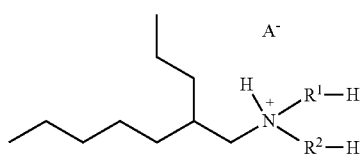

(AQ)

of the amine alkoxylate (A), where
$R^1$ and $R^2$ independently of one another are selected from the group consisting of ethylene oxide, propylene oxide, butylene oxide, and homopolymers or random or block copolymers thereof, wherein $R^1$ consists of from 1 to 30 monomer units and $R^2$ consists of from 1 to 30 monomer units, and
$A^-$ is an agriculturally acceptable anion.

2. The composition according to claim 1, wherein $A^-$ is a halide, phosphate, sulfate or anionic pesticide.

3. The composition according to claim 1, wherein, in the amine alkoxylate (A), the total number of monomers in $R^1$ and $R^2$ is from 2 to 40.

4. The composition according to claim 1, wherein the alkoxylate is the amine alkoxylate (A).

5. The composition according to claim 1, wherein the total number of monomers in $R^1$ and $R^2$ is 9 to 11.

6. The composition according to claim 1, wherein the composition further comprises a pesticide.

7. The composition according to claim 6, wherein the pesticide comprises a pesticide with at least one H-acidic group.

8. The composition according to claim 6, wherein the pesticide comprises glyphosate or glufosinate, and additionally a further pesticide.

9. The composition according to claim 1, wherein the composition further comprises glyphosate.

10. An amine alkoxylate (A)

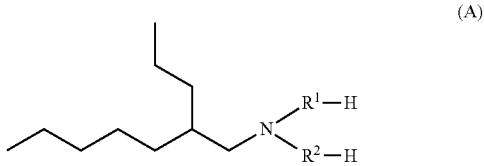

(A)

or a quaternized derivative (AQ)

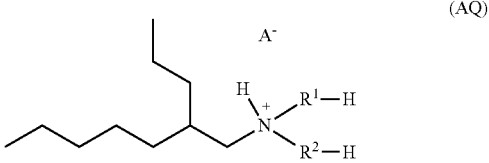

(AQ)

of the amine alkoxylate (A), where
$R^1$ and $R^2$ independently of one another are selected from the group consisting of ethylene oxide, propylene oxide, butylene oxide, and homopolymers or random or block copolymers thereof, wherein $R^1$ consists of from 1 to 30 monomer units and $R^2$ consists of from 1 to 30 monomer units, and
$A^-$ is an agriculturally acceptable anion.

11. A process for the preparation of the amine alkoxylate (A) or a quaternized derivative (AQ) of the amine alkoxylate (A) according to claim 10, comprising the alkoxylation of 2-propylheptylamine with ethylene oxide, propylene oxide, butylene oxide or a mixture thereof.

12. A method of controlling phytopathogenic fungi and/or undesired vegetation and/or undesired insect or mite attack and/or for regulating the growth of plants, wherein the composition according to claim 6, is applied on the respective pests, their environment or the plants to be protected from the respective pest, on the soil and/or on undesired plants and/or the crop plants and/or their environment.

13. A seed treated with the composition according to claim 6.

* * * * *